United States Patent [19]

Olson

[11] Patent Number: 4,901,742

[45] Date of Patent: Feb. 20, 1990

[54] DENTAL FLOSSER-DISPENSER

[76] Inventor: Mary Lou C. Olson, 1147 Ivyhill Dr., Mendota Heights, Minn. 55118

[21] Appl. No.: 187,331

[22] Filed: Apr. 28, 1988

[51] Int. Cl.⁴ ............................................. A61C 15/00
[52] U.S. Cl. ................................................... 132/325
[58] Field of Search ............... 132/323, 324, 325, 326, 132/328

[56] References Cited

U.S. PATENT DOCUMENTS

| | | | |
|---|---|---|---|
| 618,009 | 1/1899 | LaVarre | 132/323 |
| 1,110,680 | 9/1914 | Gamble | 132/323 |
| 1,512,633 | 10/1924 | Peckham | 132/326 |
| 3,747,611 | 7/1973 | Bennington | 132/325 |
| 3,747,612 | 7/1973 | Davis | 132/323 |
| 3,908,677 | 9/1975 | Beach | 132/323 |
| 3,908,678 | 9/1975 | Conn et al. | 132/323 |
| 4,178,947 | 12/1979 | McCourry et al. | 132/323 |
| 4,326,549 | 4/1982 | Hinding | 132/323 |
| 4,574,823 | 3/1986 | Uriss | 132/323 |

OTHER PUBLICATIONS

U.S. patent application Ser. No. 128,697, filed Dec. 4, 1987, "Dental Flosser Dispenser", Mary Lou C. Olson.

Primary Examiner—Robert Peshock
Attorney, Agent, or Firm—Merchant & Gould

[57] ABSTRACT

The dental flosser-dispenser includes a pistol-grip shaped handle portion and a bow portion extending therefrom for holding a length of tension of floss between its tip and an anchoring mechanism. A spool of dental floss is provided in the handle and includes a detent system for selectively paying out new floss from the spool and anchoring the spool in place while the device is being used for flossing. An alternate embodiment of the dental floss dispenser includes a pistol-grip shaped handle portion in an elongate neck portion supporting the U-shaped armature. A spool of dental floss is provided in the handle and includes a detent system for selectively paying out new floss from the spool.

5 Claims, 6 Drawing Sheets

DENTAL FLOSSER-DISPENSER

TECHNICAL FIELD OF THE INVENTION

The present invention relates generally to the field of oral hygiene, and more particularly to devices for holding and dispensing dental floss in the form of a flosser-dispenser.

BACKGROUND OF THE INVENTION

A common problem with dental floss holders is that they are difficult to manipulate in all of the necessary locations within the mouth. For example, in U.S. Pat. No. 1,110,680 to Gamble and U.S. Pat. No. 4,178,947 to McCourry et al. disclose dental floss holders which have a handle end and a floss holding end which hold a length of tensioned dental floss for use in flossing the teeth and gums. These devices, however, provide only a relatively short length of floss making it difficult to reach certain areas of the mouth and to manipulate the floss back and forth between the teeth and gums as is necessary to remove food debris or other undesirable deposits on the teeth. Moreover, these devices, like other prior art dispensing and floss holding devices, have handles and/or flossing tip structures which make them somewhat awkward and difficult to use and manipulate.

SUMMARY OF THE INVENTION

The present invention provides a dental floss dispenser and holder device which has a handle portion including a means for supporting a roll of dental floss, and a neck or barrel portion extending to a U-shaped floss holding armature portion. The floss extends up through the handle portion, through the barrel portion and is routed through the tips of the U-shaped armature whereby it is supported for flossing action. An aperture is provided in the U-shaped armature through which the end of the floss is threaded, and means are provided on the housing for anchoring the floss and for cutting it. A spool of floss is supported in the handle portion and includes detent means for selectively permitting the floss to be unwound from the spool and for holding the spool in place when desired. Accordingly, floss may be selectively unwound from the spool to provide a new length of flossing floss across the tips of the U-shaped armature. According to yet another aspect of the invention, the barrel portion and U-shaped portion include enclosed, interior hollow portions.

DETAILED DESCRIPTION OF THE INVENTION

Figure 1:
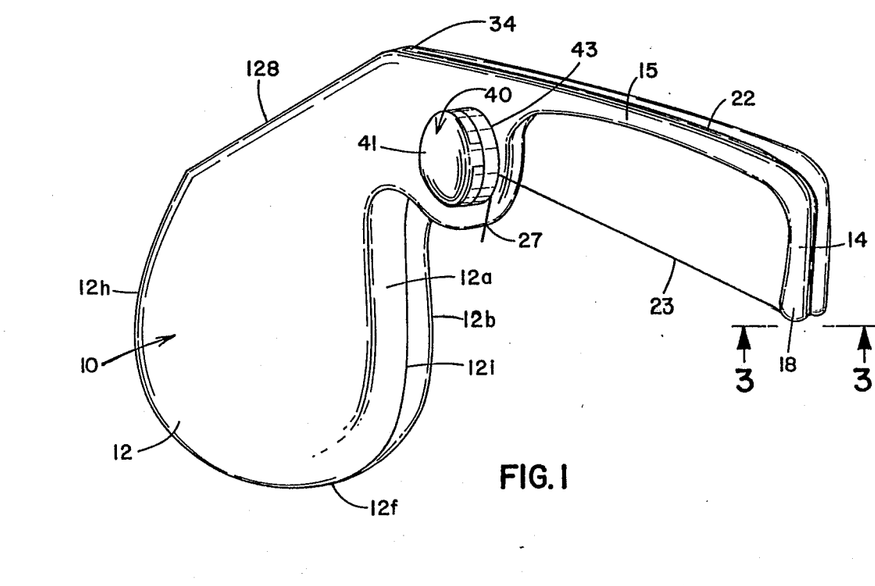
FIG. 1 is a perspective view of a prior art floss device.
Figure 2:
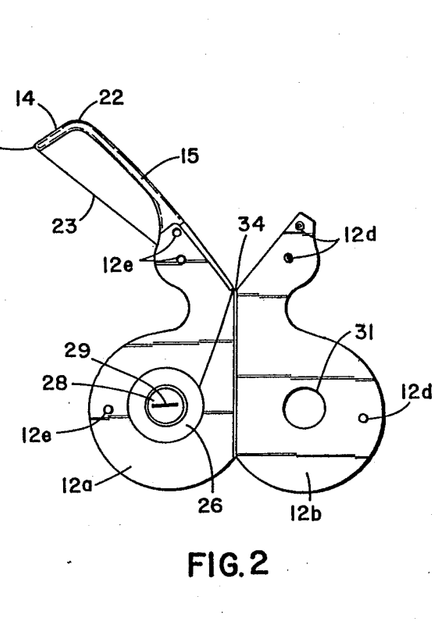
FIG. 2 is a plan view of the internal portion of the housing of the prior art dental floss device shown in FIG. 1.
Figure 3:
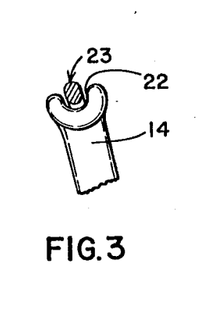
FIG. 3 is a view taken along the lines 3—3 of FIG. 1 showing the molded flossing track on the prior art device.

Referring now to FIG. 1 there is shown in perspective a view of a prior art flossing device 10. Flossing device 10 includes a housing 12 having first and second halves 12a and 12b. As best shown in FIG. 2, halves 12a and 12b are generally symmetrical in shape. Preferably, the housing 12 is molded from plastic. Construction pins 12d are provided on one side of the housing, for mating with pin receptacles 12e whereby the housing may be fastened together. As also seen in FIG. 2, housing half 12a includes an additional bow portion 14 extending therefrom. Bow 14 includes a tip 18 and an elongate back member 15. Preferably, bow 14 is resilient enough so that it bends slightly when the floss is tightened in place thereon. This resilience can thus take up any slack in the floss tension that occurs during flossing. As best seen with respect to FIG. 3, the top or back side of bow 14 includes a molded track 22 in which dental floss 23 rides. Bow 14 is preferably sized to support a 3-3½" length of floss between tip 18 and anchoring and cutting mechanism 40. The handle portion of the device 10 is preferably about 2¾-3174 " in length from bottom 12f to top 12g, 3174 -3¾" in width from back 12h to front 12i, and ½-⅞" thick.

Figure 4:
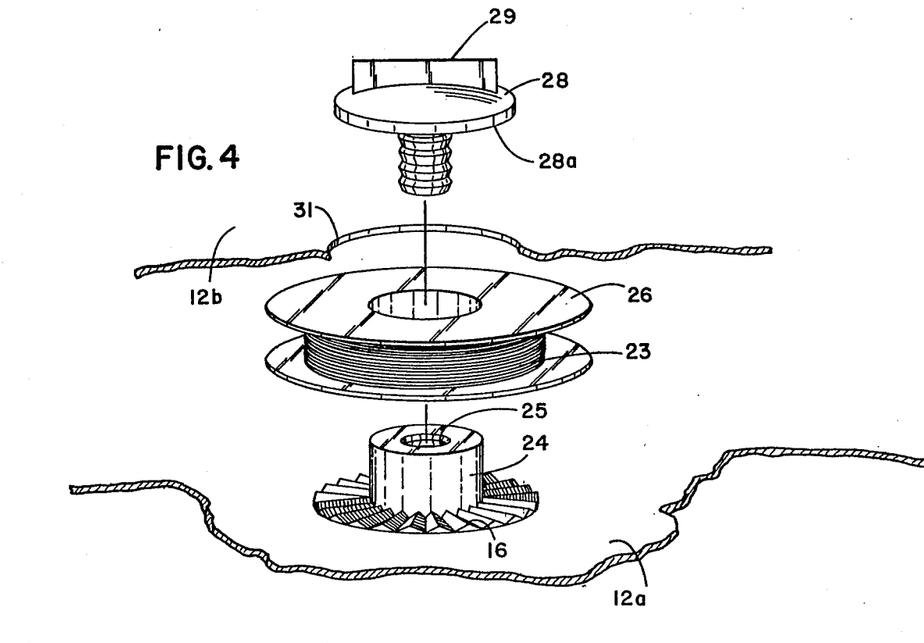
FIG. 4 is an exploded perspective view of the floss spool mechanism of the prior art flossing device.
Figure 5:
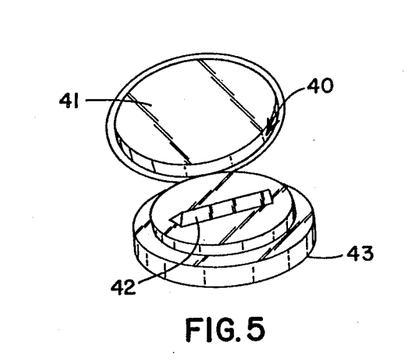
FIG. 5 is a perspective view of the anchoring and cutting mechanism of the prior art flossing device.

As may be seen in FIGS. 2 and 4, a floss dispensing mechanism 20 is mounted in the center of housing 12. Ribs 16 are molded into the interior surface of housing halve 12a and a hub member 24 with interior threads 25 extends therefrom. A spool 26 of floss 23 is positioned over hub 24 and a nut 28 with a finger-grip 29 is provided to screw into thread 25. Aperture 31 is provided in housing 12b so that finger-grip 29 is accessible from the outside of the housing for tightening and loosening the flossing spool. Aperture 31 is slightly larger in diameter than the nut 28. When the housing halves are fastened together and nut 28 is tightened down the surface of halve 12b is even with edge 28a of nut 28. As seen in FIGS. 1 and 2, floss extends from spool 26 through an opening 34 in the housing from where it follows track 22 down around tip 18 and back to a floss anchoring and cutting mechanism 40. As seen in FIG. 5, mechanism 40 includes a molded plastic cap 41 which may be flipped open to expose a sharp cutting edge 42, either metal or plastic serated edge, disposed therein. Anchor mechanism 40 is molded to housing side 12a such that a narrow annular gap or space 43 is provided between the housing wall 12a and the undersurface of anchor mechanism 40. Dental floss may be wrapped around the base of mechanism 40 and anchored thereon. In order to provide a new length of floss for use in flossing, the loose end 27 of floss 23 would be unwrapped from space 43, and nut 28 of flossing mechanism 20 would be loosened so that a new length of floss could be pulled from the spool. Once a new length of floss was extracted, nut 28 would be tightened down to anchor mechanism 40. The excess floss would then be cut off using cutting edge 42. Of course, the excess floss may be cut prior to the new length of floss being anchored.

Referring now to FIG. 6 through 11 there is shown the dental floss holding and dispensing device according to the present invention. Dispensing device 100 includes a handle portion 102 having first and second halves 102a and 102b. Handle portion 102 generally has a pistol-grip shape and a hollow interior. Handle portion 102 is sized substantially the same as the above-described handle portion of device 10, so it can be easily manipulated in the hand. Mounted in handle portion 102 for rotation is a hub number 110 which, as may be best seen in FIG. 10, includes a button portion 112 extending out through an aperture 114 in housing half 102a, and includes a hollow cylindrical interior portion 116. Hollow portion 116 is mounted on a cylindrical axle member 120 which extends into the interior of handle 102 from housing half 102b. Hub member 110 further includes four pin protrusions 122 facing toward the interior wall of housing half 102a. Housing half 102a includes four spherical cavities 124 made with pins 122 and hub member 110 is rotated into alignment therewith. Spring member 130 is mounted in the interior hollow portion of hub member 110 to spring bias hub member 110 against the inner wall of housing half 102a. Accordingly, protrusions 122 and cavity members 124 act together as detent to prevent hub 110 from rotating. The hub 110 may be rotated, however, by depressing button portion 112, thereby disengaging pins 122 from cavities 124. A spool 140 of dental floss is mounted on hub member 110, and includes floss 144 and a carrier member 142 which is interference fitted on hub member 110.

An elongate neck member or barrel portion 150 extends from handle portion 102 to a U-shaped floss holding armature 156. Preferably, armature member 156 is constructed from two molded halves 156a and 156b, while barrel portion 150 includes first and second molded halves 150a and 150b. Barrel portion 150 and floss armature 156 each include a hollow cylindrical interior portion. Floss F extends from spool 140 up through the interior of neck portion 150, down through the first side of armature 156 and out a first aperture 158 into a second aperture 159 in the other side of the armature 156. Floss F extends back up through the interior of the armature 156 and out through a third aperture 161 to the exterior of the housing. Anchoring post 165 is provided, and includes a slot 166 around one side of the base thereof around which floss F may be twisted and anchored. Mounted on the top portion of handle portion 102 is a floss cutting device 170. Device 170 includes a snap cap member 172 which may be flipped open to access a floss cutting knife member 174, which may be used to cut used lengths of floss.

Preferably, each half of device 100 is formed of molded plastic. More particularly, halves 102a, 150a, and 156a are all preferably formed of one single piece of molded plastic, while halves 102b, 150b, and 156b are formed from another piece of molded plastic. Floss cutting device 170 is preferably wholey molded on one of the two halves. Each of the halves preferably include snap fastening means by which the halves may be assembled together.

In operation, floss may be extracted from spool 140 by depressing button 112 with a finger and simultaneously pulling floss F from its end up through aperture 161 in floss armature 156. Once a suitable length of floss has been extracted from the spool, button 112 may be released, and the floss pulled until pins 122 meet with cavities 124 thereby preventing the further rotation of spool 140. The floss may then be pulled tight across the tips 163 and 164 of armature 156, and anchored on post 165. Any excess floss may be cut using device 170, and flossing device 100 is thus prepared for use. In use the device may be manipulated in the palm of the hand or with the fingers to reach all of the necessary areas in the mouth.

Figure 6:
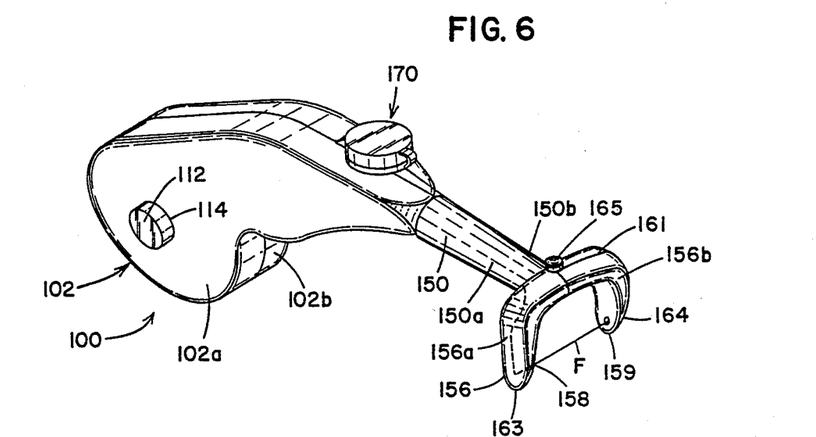
FIG. 6 is a perspective view of the dental floss holding and dispensing device according to the present invention.
Figure 7:
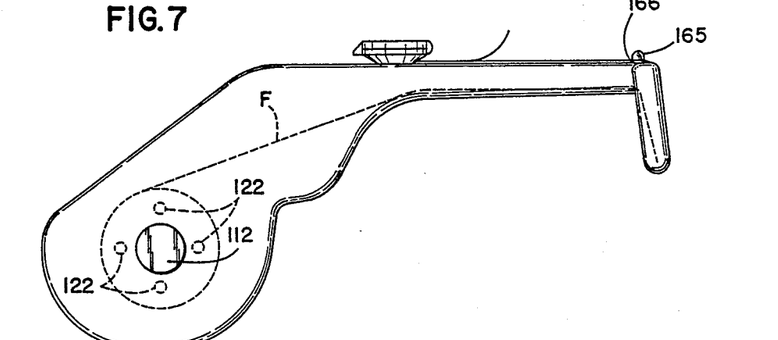
FIG. 7 is a side view of the alternative embodiment of the flossing device according to the present invention.
Figure 8:
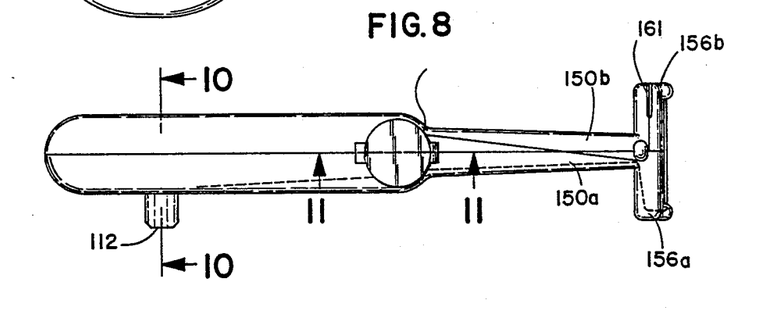
FIG. 8 is a top plan view of the flossing device according to the present invention.
Figure 9:
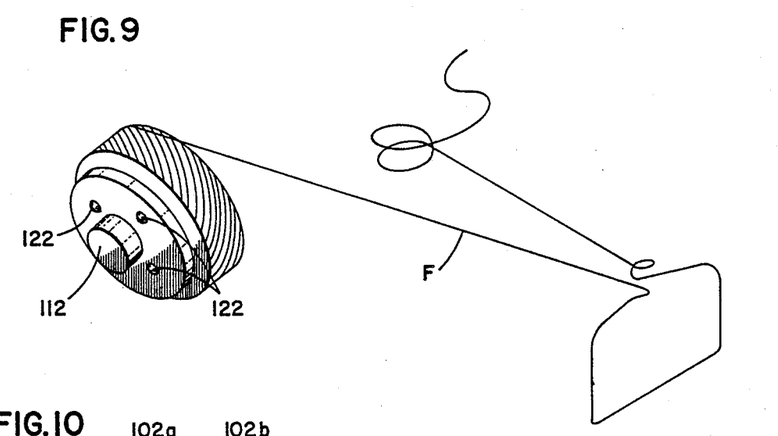
FIG. 9 is a schematic drawing showing the travel of the floss from the spool to the tip in the floss device according to the present invention.
Figure 10:
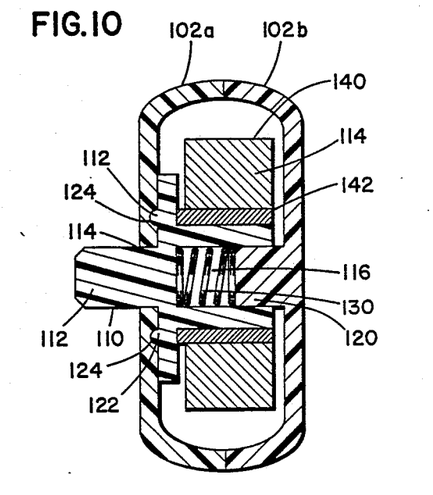
FIG. 10 is a cut away perspective view taken along the lines 10—10 of FIG. 8 showing the inner workings of the floss spool detent mechanisms according to the present invention.
Figure 11:
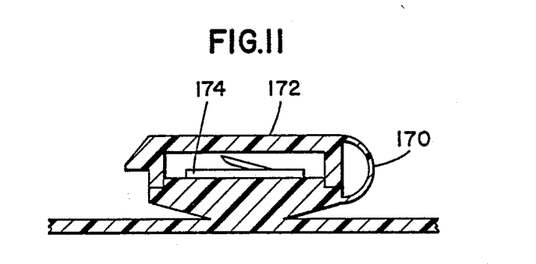
FIG. 11 is a cut away side view taken along the lines 11—11 of FIG. 8.

As may be best seen in FIGS. 6 and 8, aperture 159 and 161 are preferably large enough to permit the easy rethreading of floss F should it break during use. Thus rethreading is accomplished by pressing nob 112 to pull a new length of floss F from the spool 140, wherein the end of the floss can thus be threaded through aperture 159 and out through aperture 161.

Figure 12:
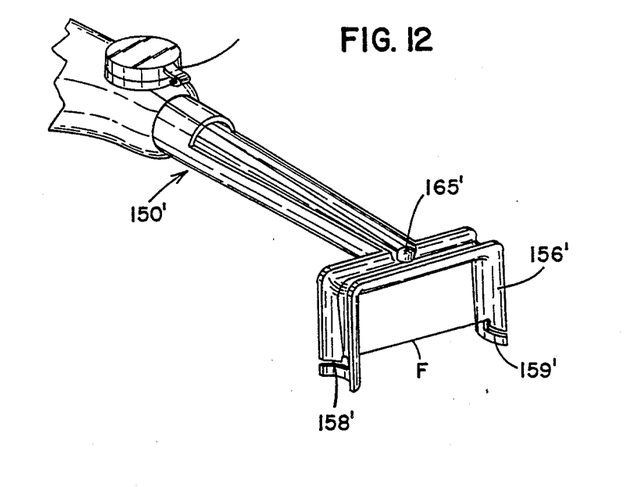
FIG. 12 is a perspective view of an alternative embodiment of the neck and U-shaped armature member of the floss device of the present invention.

Referring now to FIG. 12, there is shown an alternative embodiment of neck portion 150 and tip 156 of the embodiment of FIGS. 6-11. In the embodiment of FIG. 12, barrel portion 150' and tip 156' are cut away and open on their top halves, exposing floss F in its travel from the interior of the handle and across the tip 150'. A pair of floss guide slots 158' and 159' are provided to guide the floss between the areas of tip 156'. A post member 165' is provided to wrap floss F around from cutaway barrel portion 150' to the tip, as shown, and to anchor the floss F once drawn tight across the tip 156'. Thus, alternative embodiment barrel portion 150' and tip 156' provides free access to floss F for rethreading and floss extraction.

Thus, as described above the alternate embodiment of the present invention provides a dental floss dispensing and holding device which includes a pistol-grip shaped handle portion and a U-shaped floss holding armature member. Accordingly, device 100 according to the present invention provides a device which is easily manipulated in hand and which may be readily used to reach difficult areas in the back of the mouth. Device 100 is advantageous to prior art device 10 in that its "transverse" support of the floss to be used for flossing on the armature 156 facilities working the floss laterally and vertically between the teeth in the rear of the mouth, making flossing easier and more comfortable.

Although the invention has been described herein in its preferred form, those skilled in the art will readily recognize that various changes and modifications may be made thereto without departing from the spirit and scope of the invention as set forth in the claims appended hereto.

What is claimed is:

1. A dental floss dispensing and holding device comprising:
   a pistol-shaped housing including a hollow handle portion and a barrel portion, said handle portion sized to be gripped in the palm of a human hand, said handle portion having rotatably mounted therein a spool of dental floss;
   a floss holding a U-shaped armature member mounted on the end of said barrel portion so that the plane of the armature is generally orthogonal to said barrel portion, said armature member having first and second tips each formed to guide the floss across the tips of the armature member;

said handle portion, barrel portion, and armature portion defining a path for a length of dental floss paid out from said spool so that said floss travels from said spool through said housing, along said barrel portion, around one side of said armature, and over its tip to the other tip of said armature;

anchor means mounted on said armature for anchoring the free end of said floss;

cutting means mounted on said housing for cutting said dental floss; and detente means for selectively preventing said spool from turning whereby dental floss may be selectively paid out from said spool.

2. Apparatus according to claim 1 further wherein said barrel portion is cylindrical and has a hollow interior which opens into the interior of said housing to provide an enclosed interior path for said floss as it travels from said spool to said armature member.

3. Apparatus according to claim 2 further wherein said armature member has a generally cylindrical cross-section and an enclosed hollow interior having an opening into said barrel portion and having apertures on each said tip and further wherein said floss travels through the interior of said armature, out one of said apertures and in the other.

4. Apparatus according to claim 1 further wherein said handle portion includes a recessed area on the front side facing towards said barrel portion to provide a place where a user can nestle one or more fingers to get a grip on said housing.

5. Apparatus according to claim 1 or 4 further wherein said handle portion generally extends away from said barrel portion to form an obtuse angle between the barrel portion and the longitudinal axis of said handle portion.

* * * * *

UNITED STATES PATENT AND TRADEMARK OFFICE
CERTIFICATE OF CORRECTION

PATENT NO. : 4,901,742

DATED : February 20, 1990

INVENTOR(S) : Mary Lou C. Olson

It is certified that error appears in the above-identified patent and that said Letters Patent is hereby corrected as shown below:

Col. 2, lines 40 and 41: change "3174" to --3½--

Col. 2, line 62 change "serated" to --serrated--

Col. 3, line 67 change "wholey" to --wholly--

Signed and Sealed this

Twenty-third Day of July, 1991

Attest:

HARRY F. MANBECK, JR.

Attesting Officer

Commissioner of Patents and Trademarks